United States Patent [19]

Urdea et al.

[11] Patent Number: 4,483,964

[45] Date of Patent: Nov. 20, 1984

[54] REACTOR SYSTEM AND METHOD FOR POLYNUCLEOTIDE SYNTHESIS

[75] Inventors: Mickey S. Urdea, San Francisco, Calif.; Brian D. Warner, Eau Claire, Wis.

[73] Assignee: Chiron Corporation, Emeryville, Calif.

[21] Appl. No.: 506,153

[22] Filed: Jun. 20, 1983

[51] Int. Cl.³ .............................................. C12M 1/00
[52] U.S. Cl. ............................... 525/54.11; 525/54.1; 525/54.23; 435/287; 435/172.3; 435/317; 435/820; 435/88; 422/116; 422/131
[58] Field of Search ................... 435/87, 88, 91, 172, 435/287, 317, 820; 525/54.23, 54.1, 54.11

[56] References Cited

U.S. PATENT DOCUMENTS 4,353,989 10/1982 Bender et al. ...................... 435/317

Primary Examiner—John Kight
Assistant Examiner—Nathan M. Nutter
Attorney, Agent, or Firm—Townsend & Townsend

[57] ABSTRACT

A reactor system and method for synthesizing or degrading polynucleotides and other linear polymers includes a tubular reactor connected to a reagent manifold. The polynucleotide is immobilized on a loosely packed solid-phase support material in the tubular reactor, and reagents are sequentially introduced into the tubular reactor. After each reagent is introduced, the tubular reactor is isolated from the reagent manifold and the reagent agitated by alternately pressurizing the opposite ends of the tubular reactor. The method provides rapid and efficient synthesis of polynucleotides.

18 Claims, 1 Drawing Figure

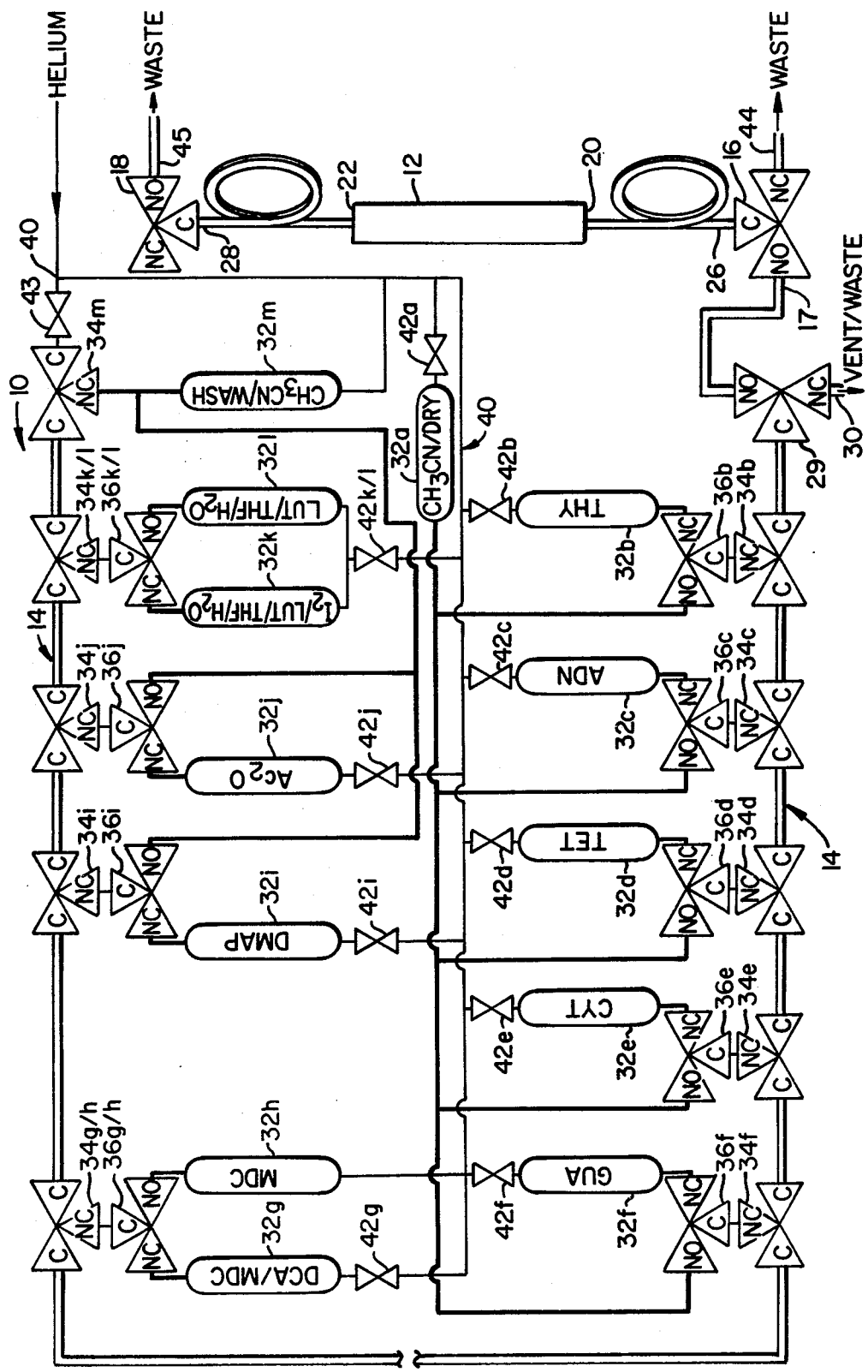

REACTOR SYSTEM AND METHOD FOR POLYNUCLEOTIDE SYNTHESIS

BACKGROUND OF THE INVENTION

1. Field of the Invention

The ability to synthesize polynucleotide fragments having a desired nucleotide sequence is a useful tool in both research and applied molecular biology. Short synthetic polynucleotides (oligonucleotides) are useful as adaptors or linkers in joining longer DNA segments, and as hybridization probes and DNA synthesis primers. Longer polynucleotides can be constructed from shorter segments having overlapping cohesive ends and used as structural genes, regulatory regions such as promoters, terminators, operators, and the like. It is thus of great interest to provide convenient automatic techniques for producing synthetic DNA fragments with high yields in a relatively short time.

At present, a variety of approaches for polynucleotide synthesis are available. These approaches can be characterized based on several criteria. First, the synthesis is usually carried out either on a solid-phase substrate or in solution. Solid-phase synthesis relies on sequential addition of mononucleotides to a growing chain attached at one end to the substrate. The solid-phase allows easy separation of the reactants, but the method requires excess quantities of reactants and usually provides only small quantities (less than 1 mg) of the desired sequence. Solution phase synthesis, while it requires lesser amounts of the expensive reagents and can provide larger quantities of the product sequence, requires isolation and purification of the intermediate product after every addition. Virtually all automated polynucleotide systems rely on solid-phase synthesis.

Second, the synthesis chemistry must be selected. There are presently two chemistries in widespread use for automated polynucleotide synthesis. The triester method, as described by Catlin and Cramer (1973) J. Org. Chem. 38:245–250 and Itakura et al. (1973) Can. J. Chem. 51:3649–3651, relies on the addition of suitably blocked phosphate-triester intermediates which are generally inexpensive and stable. The phosphite-triester method, as described by Letsinger and Lunsford (1975) J. Am. Chem. Soc. 98:3655, is somewhat more complex, but generally provides higher yields than the phosphate-triester method. The utility of the phosphite-triester method was greatly improved by the use of N,N-dialkylamino phosphites (amidites) which are more stable than the phosphorochlorodite intermediates initially employed. While the phosphite-triester method is often favored because of the greater yield at each nucleotide addition, the phosphate-triester method is also suitable for automated polynucleotide synthesis.

The third choice which must be made is the selection of a reactor system. Heretofore, solid-phase reactor systems have generally employed either (1) a tight bed column, (2) a loose bed column, or (3) a batch reactor. The tight bed column is tightly packed with the solid-phase support and the reactants are introduced either in a single pass of by a recirculating stream. Generally, such tight pack columns inhibit the mass transfer of reagents and the resulting slow diffusion rates for the reactants into the support increase the necessary reaction time and/or decrease the efficient utilization of reactants. A second problem experienced with such tight bed columns is channeling through the column packing which aggravates the mass transfer problems just discussed.

To partially alleviate these problems, loose bed columns (containing a much higher void volume than the tight bed columns) have been introduced. By slowly passing the reactant through the column, higher mass transfer rates are achieved and utilization of the expensive reactants is improved. Also, channeling is reduced since the solid phase packing will shift to equalize the flow profile therethrough. Although an improvement, the resulting mass transfer is still limited by the lack of agitation within the reactor. Moreover, the shifting of the solid phase can generate very fine particles which can plug the frits used to contain the solid phase within the reactor. This problem is also experienced by the tight bed columns, although to a lesser extent.

In a batch reactor, the support matrix is held in an enclosed vessel. Reactants are introduced and the vessel contents agitated, typically by bubbling an inert gas through the liquid in the reactor. While such a system can provide very efficient utilization of the reactants (by increasing the retention time in the reactor), relatively large volumes of the reactant and solvents are necessary to fill the reactor. Moreover, the mixing in the batch system is typically not complete, and the solid-phase support is often deposited on the vessel wall above the reagent level so that it is no longer exposed to the incoming reagents.

In addition to the above limitations, all three of the reactor systems just described suffer from bubble formation on the solid-phase substrate which inhibits the reactions and causes lower yields. The bubble formation is caused by certain solvents (in particular the methylene dichloride) which de-gas on the solid-phase substrate.

In view of the above, it would be desirable to provide a system and method for polynucleotide synthesis which would avoid or reduce the shortcomings of the prior art systems and allow the efficient utilization of process reactants with relatively short retention times for each reactant. In particular, it would be desirable to provide a reactor which affords thorough mixing of reactants to increase the mass transfer rate and which remains free from plugging.

2. Description of the Prior Art

Methods and apparatus for the automated solid-phase synthesis of polynucleotides are described in U.S. Pat. No. 4,373,071 to Itakura; European Patent Application No. 81101449.5; and in Alvarado-Urbina et al. (1981) Science 214:270–274. Automated systems for the synthesis of polynucleotides are available from Biosearch, San Rafael, California; Bio Logicals, Toronto, Canada; Applied Biosystems, Foster City, California; and Bethesda Research Laboratories, Inc., Gaithersburg, Maryland. These systems and others generally rely on the synthesis techniques described above.

SUMMARY OF THE INVENTION

The present invention provides a method and system for the sequential modification of a linear polymeric molecule attached to a dispersed solid-phase support, as exemplified by the addition of individual nucleotides in a predetermined order to a nucleotide chain. The dispersed solid-phase is retained within a reactor zone which is provided with at least two access ports for the introduction and removal of reagents. Reagents are selectively delivered to the reactor zone through at least one of the access ports by a reagent manifold.

After a predetermined amount of reagent has been introduced, the reactor zone is isolated from the reagent manifold and the reagent agitated within the zone by inducing a reversing flow of the reagent through the two access ports.

The subject method and system provide highly efficient reactant utilization with relatively short retention time when compared with the reactors of the prior art. In particular, by providing a relatively loosed packed column, efficient agitation of the solid-phase support is achieved without channeling and inhibition of mass transfer. Moreover, the reversing flow of reactants and wash solutions help prevent plugging of the access ports of the reactor zone.

BRIEF DESCRIPTION OF THE DRAWINGS

The FIGURE is a schematic representation of the reactor system including the reactor and reagent delivery apparatus of the present invention where NO indicates a normally open port, NC indicates a normally closed port, and C indicates a common port.

DESCRIPTION OF THE SPECIFIC EMBODIMENTS

The reactor system including both the reactor and the reagent delivery apparatus of the present invention is broadly applicable to a wide variety of chemical synthesis and degradation techniques which result in modification of a linear polymeric molecule attached to a dispersed solid phase substrate or support. The reactor system can be used with a wide variety of well known chemical methodologies where the attachment of the polymeric molecule to the solid-phase substrate facilitates separation of the molecule from liquid phase reactants. Thus, the reactor system will find its greatest use in stepwise reactions which require precise and repeated separation of a polymeric material comprising a plurality of units in predetermined order from liquid phase reactants. In particular, the reactor system will find use in the stepwise formation or degradation of linear polymeric materials, such as proteins (poly(amino acids)) and polynucleotides, e.g. either poly(deoxyribonucleotides), i.e., DNA, or poly(ribonucleotides), i.e., RNA, or derivatives thereof, e.g. substituted bases, where the polymeric chains are attached to an insoluble macroscopic solid-phase support. The design of the reagent delivery system is such that with minor modifications to the "plumbing" (arrangements of tubing and valves) and adjustments to the control elements, several reactors could be fitted to the reagent delivery system so that more than one polymer could be synthesized (or degraded) simultaneously. It should also be possible to incorporate systems for detection, monitoring and control of the reaction(s) as adjuncts to the device. It may also prove possible to purify oligomers while they remain bound to a solid-phase support. This process would take advantage of chemical differences between the desired product and "failure", i.e., abortive or incomplete, sequences (e.g. the presence of the 5'-dimethoxytrityl group in the present embodiment of oligonucleotide synthesis).

The remainder of this description will be directed primarily to the synthesis of polynucleotides, but it will be appreciated by those skilled in the art that the reactor system would require only minor modification for use in protein synthesis, protein sequencing, carbohydrate synthesis, nucleotide sequencing, and the like. Methods to achieve these syntheses and degrations are well known. Exemplary references include: Edman and Henschen (1975) *Protein Sequence Determination*, Springer-Verlag, Berlin, p. 232; Stewart, J. M. and Young, J. D. (1969) *Solid Phase Peptide Synthesis*, Freeman and Co., San Francisco; and Tu and Wu (1980) Methods Enzymol. 65:620.

The reactor system of the present invention comprises a reactor zone which is connected to a reagent manifold capable of selectively delivering the reagents necessary for a particular reaction to the reactor zone. The reactor zone includes at least two access ports having porous barriers to contain the dispersed solid-phase support material, and reagents are delivered to the reactor zone through either or both of the barriers. Means are provided for isolating the reactor zone from the reagent manifold and for inducing a reversing flow of reactants through the reactor zone, typically by applying pressure alternatively at each access port. The oscillating or reversing flow provides a thorough yet gentle agitation of the dispersed solid-phase support and the reactants.

Conveniently, the reactor zone comprises an elongate tube or column which is open at each end. The cross-section of the reactor will usually be circular although this is not necessary, and the dimensions of the reactor are not critical. Most often, it will be desirable to minimize the volume of the reactor to reduce the usage of reagents, which reagents can be very expensive. The reactor is always kept totally full of liquid reagent during agitation; the cross-sectional area should not affect flow properties. Also, the cross-sectional area of the tube or column should not be so large that plug flow of reactants under pressurization is prevented. Conveniently, the reactor column will have an inside diameter in the range from about 0.1 to 1.0 cm, usually from about 0.1 to 0.5 cm. The length of the reactor column can vary even more widely, usually being at least 1.0 cm with no upper limit, more usually being about from 1.0 cm to 25 cm. For the synthesis of polynucleotides, a reactor having a length of 5 cm and an internal diameter of 0.3 cm (with a resulting volume of 300 µl) has been found suitable. For protein synthesis, the reactor dimensions will generally be greater, usually being 500 µl or larger. The reactor structural material is not critical, with glass, stainless steel or other inert materials being suitable.

The reactor column is enclosed at either end by porous barriers, such as glass, Teflon ®, or stainless steel frits. The pores in the barriers must be sufficiently fine to retain the dispersed solid-phase support within the reactor, yet be sufficiently large to allow introduction and removal of liquid phase reagents without excessive pressure requirements. For a dispersed solid-phasse having particle dimensions in the range from 5 to 50 µm, suitable materials for the barriers include those mentioned above available from Omnifit, Atlantic Beach, N.Y. The construction of the reactor column and frits is conventional and need not be further described.

The solid-phase support will typically be comprised of small porous beads or particles in the form of a resin or gel. Numerous materials are suitable as solid-phase supports for the synthesis and/or degradation of polynucleotides and polypeptides. In general, such supports should provide good mass transfer in and out of their pores, be chemically inert, be minimally affected by reagents and solvents, and allow derivatization, attachment and removal of the polymeric material of interest. Preferred solid-phase materials include polystyrene derivatives, controlled pore glass, aluminum oxide beads, and silica beads. Particularly, preferred is Fractosil®, a silica product available from Merck. The size of the solid-phase beads may vary from about 5 to 50 μm, with the larger beads being preferred. The Fractosil® beads have an average size of about 40 μm; nucleoside derivatized Fractosil® is available from Biosearch.

In order to enhance mixing and mass transfer within the reactor column, it is desirable that the solid-phase support material be loosely packed. By loosely packed, it is meant simply that the solid-phase beads will be a slurry or suspension, not to exceed 50% w/v, able to shift positions under the influence of the reversing flow of reagent and wash solutions. During the oscillatory or reversed flow action, mentioned above and described in detail below, the solid-phase support will successively and repeatedly undergo transitions from a loosely packed column (upward flow) to a more tightly packed column (upward flow) to an agitated suspension or slurry (w/v≦50%) to a loosly packed column (downward flow) to a more tightly packed column (downward flow) and the reverse. Thus, the present invention provides aspects and advantages, without the shortcomings, of both a loose bed and tight bed column, and batch reactor simultaneously.

Referring now to the FIGURE, a particular system employing the present invention for the synthesis of polynucleotides will be described. The system employs the deoxynucleotide phosphoramidite method first described by Beaucage and Caruthers (1981) Tet. Lett. 22:1859–1862. Although the term nucleotide generally refers to the phosphate oxidation state, as used herein it will be understood to mean either phosphite- or phosphate-containing nucleoside. This approach is a variation of the phosphite-triester method described hereinbefore. With suitable modification, however, the system of the present invention could easily be adapted to the phosphate-triester method, or virtually any other solid-phase polynucleotide synthesis method.

The reactor system 10 includes a reactor column 12 and a reagent manifold 14. The reactor column 12 is a glass tube having an inside diameter of 0.3 cm and a length of 5.0 cm, resulting in a reactor volume of 300 μl. Teflon® frits (25 μm pore size) 20 and 22 are attached at each end to provide porous barrers for the introduction and removal or reactants. No other ports are provided.

The reactor column 12 is separated from the reagent manifold 14 by an isolation valve 16 and from an inert gas manifold 40 by isolation valve 18. The first isolation valve 16 is connected to porous barrier 20 by a conduit 26, while the second isolation valve 18 is connected to porous barrier 22 by a conduit 28. The conduits 26, 28 are flexible tubing formed from an inert material, such as Teflon® or Kel-F®. The diameter of the tubing will depend on the reactor volume and volume of reagents being transferred. Generally, inside diameters in the range from 0.5 to 1.5 mm will be suitable.

For reasons that will be described hereinafter, it is desirable that the conduits 26 and 28 provide a surge volume intermediate the isolation valves 16, 18 and the reactor column 12 at least equal to the volume of the reactor column 12. Conveniently, such surge volume can be provided by coiling a predetermined length of the tubing of conduits 26 and 28. Alternatively, the wall of the reactor column 12 could be extended beyond the barriers 20, 22 to provide the necessary additional volume.

The isolation valves 16 and 18 are three-way, two-position automatic valves, typically solenoid-operated valves. The first isolation valve 16 is connected at the common port to conduit 26, as just described. The normally open port of valve 16 is connected to the reagent manifold 14 by a conduit 17, and the normally closed port is connected to a lower waste discharge line 44. The second isolation valve 18 is similarly connected at the common port to conduit 28 and at the normally open port to the upper waste discharge line 45. The normally closed port of valve 18 is connected to the inert gas manifold 40.

The waste valve 29 is also a three-way, two-position automatic valve and has common and normally open ports connected to the reagent manifold 14 and conduit 17, respectively. The normally closed port is directed through conduit 30 to a drain or waste reservoir (not shown). In the de-energized position, reagent manifold 14 is connected to the reactor column 12 through conduits 17, 26 and valve 16. In the energized position, the reagent manifold 14 is open to conduit 30, the vent/waste port.

The reagent manifold 14 connects a number of reagent and wash solution supply reservoirs 32 to the reactor column 12 through valves 16 and 29. Generally, the supply reservoirs 32 are connected to the reagent manifold 14 in pairs comprising one reagent and one wash solution. For example, reservoir 32a holds dry acetonitrile wash solution which is connected in parallel with a number of the reagents, including the N,N-dimethylaminophosphoramidites corresponding to the four nucleotide bases, where THY is thymine, ADN is adenine, CYT is cytosine, and GUA is guanine (reservoirs 32b, c, e, and f, respectively) and tetrazole (TET, reservoir 32d). Others of the reagents are individually paired with wash solution, as required. Dichloroacetic acid/methylene dichloride (DCA/MDC, reservoir 32g) is paired with a wash solution of methylene dichloride (MDC, reservoir 32h), and iodine in lutidine/tetrahydrofuran/water ($I_2$/LUT/THF/$H_2O$, reservoir 32k) is paired with a wash solution of lutidine/tetrahydrofuran/water (LUT/THF/$H_2O$, reservoir 32l).

Each of the reagent/wash solution pairs is connected to the reagent manifold 14 at a single entry point. It is preferred to make connection with a pair of valves in series. Referring, for example, to the connection of reservoirs 32a and 32b, a first two-way valve with common port 34b is connected in the reagent manifold 14, while a three-way valve 36b receives the protected nucleotide (thymidine) through a normally closed port and the acetonitrile wash solution through a normally open port. The three-way valve has two positions and acts as a selector in directing either the protected nucleotide or the wash solution to the first valve 34b. Valves 34 have two ports that are always open and in common with the reagent manifold 14, and one normally closed position such that when the valve is energized, it directs the flow of either the protected thymidine or the wash solution to the reagent manifold 14. Although valve 34 will not block the flow of reagents to or from upstream (more remote from the reactor 12) when it is opened to flow from valve 36, this presents no operational problem due to the way the reagents are positioned along the reagent manifold 14. The reagent manifold 14 is thoroughly washed between synthetic steps by wash acetonitrile (reservoir 32m) which is the reagent most remote from the reactor 12. Also, since the system is open beyond the reactor through valve 18 and conduit 45, the flow of reagents is directed through the reactor 12 and no appreciable flow of reagents in the opposite direction occurs.

Each of the remaining reagent/wash solution pairs is similarly arranged with three-way and two-way common port valves 36 and 34, respectively. Although it would be possible to employ four-way, three-position valves, the use of a pair of valves, as just described has certain advantages. First, leakage of the reagent or wash solution is less likely because of two blocking valves in series, rather than a single blocking valve. This is an advantage because even trace amounts of certain of the reagents, if introduced at the wrong time during synthesis, will destroy labile reactants and/or the product and halt the synthesis. Second, since the wash solutions are directed through the valving after the active reagents, the liquid in the short conduit between and in the valves 34 and 36 will be wash solution. Thus, even if a small amount of leakage occurs across the first valve 34, the wash solutions are generally not harmful to the synthesis. Also, leakage of solutions from the common or normally closed position of valves 36 into the reservoirs 32 will not result in the loss of stored reactants, since the material will be wash solutions which are miscible and non-reactive.

The flow of reagent and wash solutions through the reactor system is initiated by pressurization of each of the reservoirs 32 with an inert gas, typically helium. To this end, the helium manifold 40 is provided which supplies a constant positive pressure, typically from about 5 to 15 psig, to each of the reservoirs. The pressurization of each reservoir is individually controlled by two-way valves 42 which also isolate one reservoir from another. This is necessary since the reagent vapor pressures are sufficiently high to cause both unwanted chemical reactions to occur in the helium manifold 40 and contamination, and potentially inactivation, of the reagent solutions. In addition to being connected to each of the reservoirs 32, the helium manifold 40 is connected through a blocking valve 43 to the end of the reagent manifold 14 remote from the reactor column 12. Finally, the helium manifold 40 is connected to one end of the reactor column 12 through isolation valve 18 and to the other via the reagent manifold 14 and valves 29 and 16.

All valves in the system are capable of automatic actuation, typically being solenoid or other electrically-operated valves. In this way, the system can be automatically operated from a central controller, typically a programmable microcomputer or other controller capable of the sequential actuation of the valves in a predetermined order. In order to reduce the total volume of reagents used by the system, avoid entrapment of reagents within the valves and minimize the cycling time between nucleotide additions, it is desirable that the valves have a low internal volume and a short actuation time. "Series 2" and "Series 3" solenoid valves available from General Valve Corporation, East Hanover, New Jersey are suitable for the system of the specific embodiment.

In operation, the reactor column 12 is first removed from the system 10 and loaded with a suitable solid-phase support which has previously been derivatized with a desired nucleoside. Such derivatized supports may be obtained commercially from vendors such as Applied Biosystems, Inc., Foster City, Calif.; Vega Biochemicals, Tucson, Ariz. and others.

After reconnecting the reactor column 12 to the conduits 26 and 28, the reactor system will be flushed with a wash solution, typically acetonitrile. The reactor system is then ready for the addition of nucleotides to the support. The procedure which will be described is as found in co-pending application Ser. No. 457,412. In general, the procedure consists of four basic reaction steps with intermediate washing steps. The reactions are (1) detritylation, (2) condensation with the desired phosphoramidite (3) blocking unreacted hydroxyl groups with acetic anhydride and dimethylaminopyridine, and (4) oxidation of the phosphite to the phosphate with iodine. After the desired chain sequence is synthesized, the resulting polynucleotide will be released from the solid-phase support, treated to remove the protecting groups, purified, and sequenced to assure that the proper structure has been obtained.

A more detailed description of the operation of the reactor system of the present invention will be made in reference to the timing chart shown in Table 1. The first step in each successive addition of a nucleotide is the removal of the dimethoxytrityl(di-p-anisylphenylmethyl) blocking group present on the 5'-hydroxyl of the last nucleotide added to the chain. The step, referred to as detritylation, is accomplished by introducing a mixture of dichloroacetic acid (DCA) and methylene dichloride (MDC) from reservoir 32g. The DCA/MDC is introduced through valves 34g/h, 36g/h as described previously.

TABLE 1

| Step | Description | Reagent | Reservoir | Repetitions | Time/Repetition | Total Step Time |
|---|---|---|---|---|---|---|
| 1 | Wash | MDC | 32h | 2 | 15 sec | 30 sec |
| 2 | Detritylation | DCA/MDC | 32g | 3 | 60 sec | 180 sec |
| 3 | Wash | MDC | 32h | 2 | 15 sec | 30 sec |
| 4 | Wash | $CH_3CN$(wash) | 32m | 2 | 15 sec | 30 sec |
| 5 | Wash | $CH_3CN$(dry) | 32a | 3 | 15 sec | 45 sec |
| 6 | Condensation | Tetrazole | 32d | 3 | 45 sec | 135 sec |
|   |   | Amidite | 32b, c, e or f |   |   |   |
| 7 | Wash | $CH_3CN$(dry) | 32a | 1 | 15 sec | 15 sec |
| 8 | Wash | $CH_3CN$(wash) | 32m | 2 | 15 sec | 30 sec |
| 9 | Capping | DMAP | 32i | 2 | 45 sec | 90 sec |
|   |   | $Ac_2O$ | 32j |   |   |   |
| 10 | Wash | $CH_3CN$(wash) | 32m | 1 | 15 sec | 15 sec |
| 11 | Wash | LUT/THF/$H_2O$ | 32l | 1 | 20 sec | 20 sec |
| 12 | Oxidation | $I_2$/LUT/THF/$H_2O$ | 32k | 1 | 20 sec | 20 sec |
| 13 | Wash | LUT/THF/$H_2O$ | 32l | 3 | 20 sec | 60 sec |
| 14 | Wash | $CH_3CN$(wash) | 32m | 3 | 15 sec | 45 sec |

Total Cycle Time 12 min 25 sec

Sufficient reagent is introduced so that conduit 26 and reactor 12 are filled, with conduit 28 remaining substantially empty. This filling can be accomplished by opening valves 34g/h and 36g/h for a measured period of time, typically 5 to 7 seconds.

After filling, the valves 16, 43 and then 18 are alternately actuated so that helium pressure from helium manifold 40 is applied in turn to each end of the reactor column 12. With a column volume of 300 μl and helium pressure at 10 psig, a frequency in the range of from about 1 to 10 Hz, usually about 1 to 5 Hz, is suitable to provide efficient mixing of the solid and liquid phases as a suspension or slurry. Agitation can be continued as long as desired; usually any helium bubbles that adhere to the solid-phase support are shaken off after about 5–10 seconds. This is necessary since gas bubbles adhering to the solid-phase support would interfere with the reactions taking place at or near the support surface. For detritylation, agitation is continued for approximately 60 seconds, after which time the column 12 is drained through the upper waste line 45. The detritylation step is then repeated with fresh DCA/MDC two times for a total of three repetitions.

After detritylation, the reactor column 12 is washed twice with methylene dichloride (MDC). The methylene dichloride is introduced through the column through the same valves 34g/h, 36g/h as the DCA/MDC. In this way, complete washing of the valves 34g/h, 36g/h and the manifold is assured and trace contamination avoided. When any reagent is introduced into reagent manifold 14 through a valve 34, a small portion may flow in the manifold 14 distal to the valve 34, with reference to the reactor 12, due to compression of the column of helium gas in manifold 14; however, it can be flushed through reagent manifold 14 to the waste discharge line 44 by activation of valves 43 and 16 during the next agitation cycle.

The reactor column 12 is then washed twice with wash acetonitrile from reservoir 32m and three times with dry acetonitrile (reservoir 32a). Each washing step is of 15 seconds duration. A portion of the reagent is first routed through the vent/waste port 30 prior to being diverted to the column 12. This ensures that contaminants in the reagent manifold 14 do not reach the reactor. The waste discharge line is used throughout the synthesis whenever reagent integrity is critical.

The nucleotide chain is now ready for the addition of the next nucleotide. The desired phosphoramidite and tetrazole are first selected by alternately energizing the appropriate three-way valves 36 (b,c,e or f and d, respectively). These reagents are then metered (measured) out in equal volumes by alternate energization of the related two-way valves with common port 34 (b,c,e, or f and d) for approximately 200 msec. each. In this way the stream of reagent entering the column 12 is almost completely mixed. It is also possible to aliquot more than one phosphoramidite simultaneously, which thus permits, e.g. the synthesis of degenerate hybridization probes. The condensation reaction is carried out for 45 seconds, with the reversing flow agitation as described before. Two repetitions of 45 seconds each are performed.

The reactor column 12 is next washed with one 15 second treatment of dry acetonitrile from reservoir 32a. The acetonitrile will be introduced through valves 34d, 36d and the valves 34, 36 associated with the reservoir 32b, 32c, 32e, or 32f from which the nucleotide amidite was just introduced. The manifold 14 and reactor 12 are then exposed to wash acetonitrile from reservoir 32m.

Before proceeding with oxidation of the phosphite to the phosphate, the unreacted nucleotide chain with a terminal phosphate remaining from the previous cycle is capped using dimethylaminopyridine (DMAP) from reservoir 32i and acetic anhydride (Ac₂O) from reservoir 32j. The capping reaction, which thus removes undesired, abortive reaction products, is performed twice for 45 seconds. The column is then washed twice for 15 seconds with wash acetonitrile from reservoir 32m directed through valves 34, 36 associated with each reservoir 32i and 32j. A second washing step with LUT/THF/H₂O from reservoir 32l is performed for 20 seconds.

The oxidation of the phosphite to phosphate is then performed using iodine in LUT/THF/H₂O from reservoir 32k. The oxidation requires only one repetition of 20 seconds, and is followed by three wash cycles (20 seconds each) with LUT/THF/H₂O from reservoir 32l.

Prior to beginning the next nucleotide addition cycle, the column is washed with wash acetonitrile (reservoir 32m) three times (15 seconds each). The steps 1–14 (Table 1) require a cycle time of approximately 12 minutes, 25 seconds, and will be repeated for each nucleotide which is added to the nucleotide chain.

At the end of the synthesis, the solid-phase support is removed from the reactor column 12 and the polynucleotide may be recovered by conventional techniques. For example, the covalent link between the polynucleotide and the support may be hydrolyzed with ammonia at room temperature. After separating the support by filtration or centrifugation, the filtrate may be further deblocked at elevated temperature. A subsequent acid deprotection of the 5'-dimethoxytrityl group may or may not be desirable at this point. The polynucleotide may then be purified by high-performance liquid chromatography or by electrophoresis on polyacrylamide gels.

Although the foregoing invention has been described in some detail by way of illustration and example for purposes of clarity and understanding, it will be obvious that certain changes and modifications may be practiced within the scope of the appended claims.

What is claimed is:

1. A reactor system for the sequential modification of a linear polymer attached to a dispersed solid-phase support, said reactor system comprising:

a reactor zone for holding said dispersed solid-phase support, said reactor zone having at least two access ports defined by porous barriers;

a reagent manifold for selectively delivering particular reagents to the reactor zone through at least one of said porous barriers; and means for blocking the flow of reagents to the reactor zone from the reagent manifold; and means for inducing a continuously reversing flow of reagent through said reactor zone when the flow of reagents is blocked from the reagent manifold, whereby the reagent previously fed to the reaction zone can be agitated without recycling through the reagent manifold.

2. A reactor system as in claim 1, wherein the reactor zone is defined by an elongate tubular column which is open at both ends, said open ends defining the access ports and having the porous barriers thereacross.

3. A reactor system as in claim 1, further including a surge volume at each end of the reactor zone.

4. A reactor system as in claim 1, wherein the means for inducing a continuously reversing flow of reagents includes means for supplying a pressurized inert gas and means for directing said pressurized inert gas alternately to both of said access ports.

5. A reactor system as in claim 1, wherein the means for blocking and means for inducing includes first and second isolation valves selectively capable of (a) directing reagents to the reactor, (b) pressurizing the reactor, and (c) venting the reactor.

6. A reactor system as in claim 5, wherein the means for isolating and means for inducing further include surge volume between each isolation valve and the reactor zone, said surge volume being at least equal to the volume of the reactor zone.

7. A reactor system for the sequential modification of a linear polymer attached to a dispersed solid-phase support, said system comprising:
- a tubular reactor for holding said solid-phase support, said reactor being enclosed at each end by a porous barrier;
- a plurality of reagent reservoirs and wash reservoirs, at least some of said reagent and wash reservoirs being arranged in pairs;
- a reagent manifold having a plurality of entry ports for receiving reagents and wash solutions from said reservoirs, and at least one outlet for directing said reagents and wash solutions to the reactor, wherein said pairs of reagents and wash solutions each enter the manifold through common entry ports; and
- means for blocking the flow of reagents to the reactor from the reagent manifold and for alternately pressurizing the two opposite ends of the reactor to induce a reversing flow of previously-introduced reagents or wash solutions therethrough.

8. A reactor system as in claim 7, wherein the pairs of reagents and wash solutions are connected to their respective entry ports through common valves to assure that the reagent is completely washed from the manifold.

9. A reactor system as in claim 8, wherein each reagent and wash solution pair is connected to the manifold through two valves in series.

10. A reactor system as in claim 9, wherein the two valves in series include a two-way common port valve connected to the entry port in the reagent manifold and a three-way valve connected to selectively direct either reagent or wash solution to the two-way valve.

11. A reactor system as in claim 7, wherein the reagent and wash reservoirs are capable of being pressurized to induce flow of reagent and wash solutions through the manifold to the reactor zone.

12. A reactor system as in claim 7, further comprising a control system for selectively directing reagent and wash solutions to the reactor zone, blocking the flow of reagents to the reactor zone, and pressurizing the reactor zone to induce a reversing flow of reagents or wash solutions therethrough.

13. A reactor system as in claim 11, further including means for selectively pressurizing the reagents and wash reservoirs to deliver reagent and wash solutions to the reactor zone through the reagent manifold.

14. A reactor system as in claim 13, wherein the pressurizing means further includes means for isolating the reservoirs from each other to prevent cross contamination.

15. A method for synthesizing polynucleotides by selectively introducing reagents to a solid-phase substrate in a tubular reactor zone whereby individual nucleotides are sequentially added to a chain of nucleotides attached to said substrate, said method characterized by retaining at least some of the reagents within the reactor zone and inducing an oscillating flow of reagents by alternately pressurizing each side of the reactor.

16. A method for synthesizing polynucleotides as in claim 15, wherein the flow of reactants is reversed at a frequency from 1 to 10 Hz.

17. A method for synthesizing polynucleotides as in claim 15, wherein the oscillating flow of reagents is induced by alternately pressurizing each side of the reactor, with an inert gas.

18. A method as in claim 17, wherein the inert gas is helium.

* * * * *